(12) United States Patent
Vedrine

(10) Patent No.: US 9,480,804 B2
(45) Date of Patent: Nov. 1, 2016

(54) MONODOSE NASAL DRUG DELIVERY SYSTEM

(75) Inventor: Lionel Vedrine, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1120 days.

(21) Appl. No.: 13/517,496

(22) PCT Filed: Dec. 23, 2010

(86) PCT No.: PCT/US2010/062029
§ 371 (c)(1),
(2), (4) Date: Aug. 14, 2012

(87) PCT Pub. No.: WO2011/079278
PCT Pub. Date: Jun. 30, 2011

(65) Prior Publication Data
US 2012/0302966 A1    Nov. 29, 2012

Related U.S. Application Data

(60) Provisional application No. 61/284,696, filed on Dec. 23, 2009.

(51) Int. Cl.
*A61M 11/00* (2006.01)
*A61M 15/08* (2006.01)
(Continued)

(52) U.S. Cl.
CPC ............ *A61M 15/08* (2013.01); *A61M 11/007* (2014.02); *A61M 5/282* (2013.01); *B05B 11/02* (2013.01)

(58) Field of Classification Search
CPC .. A61M 11/007; A61M 15/08; A61M 5/282; B05B 11/02

USPC .................................................. 604/207, 218
See application file for complete search history.

(56) References Cited

U.S. PATENT DOCUMENTS 4,962,868 A * 10/1990 Borchard ............... A61M 11/06
                                                        128/200.14
5,501,373 A    3/1996  Galli
5,984,899 A   11/1999  D'Alessio et al.
(Continued)

FOREIGN PATENT DOCUMENTS

JP    2001-137355    5/2001
JP    2001-526097   12/2001
(Continued)

OTHER PUBLICATIONS

English Translation of Chinese Office Action dated Sep. 12, 2013 issued in corresponding foreign application No. 201080063063.1.
(Continued)

*Primary Examiner* — Theodore Stigell
(74) *Attorney, Agent, or Firm* — The Webb Law Firm

(57) ABSTRACT

A delivery device for delivery of a medicament to a user including a container defining a reservoir storing the medicament, a body in which the container is received, a spray nozzle arranged on one of the body and the container for receiving medicament expelled from the container, and a pusher actuatable for pushing the medicament from the container reservoir through the nozzle, said pusher being movable from a rest position to a fully activated position relative to said body in response to an actuating force. The assembly is particularly applicable to nasal syringes where it is desirable to deliver the medicament in the form of a spray.

19 Claims, 9 Drawing Sheets

(51) Int. Cl.
*A61M 5/28* (2006.01)
*B05B 11/02* (2006.01)

(56) References Cited

U.S. PATENT DOCUMENTS

| | | |
|---|---|---|
| 6,382,465 B1 | 5/2002 | Greiner-Perth |
| 6,622,721 B2 | 9/2003 | Vedrine et al. |
| 7,296,566 B2 | 11/2007 | Alchas |
| 2005/0098172 A1 | 5/2005 | Anderson |
| 2006/0124778 A1* | 6/2006 | Vendrine ............ A61M 5/2429 239/602 |
| 2007/0131717 A1 | 6/2007 | Davies et al. |
| 2007/0131721 A1 | 6/2007 | Fritschi et al. |
| 2008/0033359 A1 | 2/2008 | Kazemzadeh |
| 2008/0210229 A1 | 9/2008 | Corbacho |

FOREIGN PATENT DOCUMENTS

| | | |
|---|---|---|
| JP | 2006-500134 | 1/2006 |
| JP | 2007-510448 | 4/2007 |
| JP | 2008-538706 | 11/2008 |
| WO | WO 2009/057572 | 5/2009 |

OTHER PUBLICATIONS

English Translation of Chinese Office Action dated Jun. 13, 2014 issued in corresponding foreign application No. 201080063063.1.

International Preliminary Report on Patentability dated Jul. 5, 2012 issued in corresponding application No. PCT/US2010/062029.

* cited by examiner

MONODOSE NASAL DRUG DELIVERY SYSTEM

RELATED APPLICATIONS

This is a U.S. national stage of application No. PCT/US2010/062029, filed on Dec. 23, 2010. Priority is claimed on the following application: U.S. Application No.: 61/284,696 filed on Dec. 23, 2009, the disclosure contents of which is hereby incorporated here by reference.

BACKGROUND OF THE INVENTION

1. Field of the Invention

The present invention relates to a medical device including a nasal delivery device for delivering a medicament in the form of a spray intranasally.

2. Description of the Related Art

Delivery of a medicament as a spray through a nasal passageway is the optimal mode of delivery for certain liquid medicaments. To accomplish this, a spray nozzle is arranged at one end of a container such as, for example, the spray nozzle disclosed in U.S. Pat. No. 7,296,566 to Alchas and U.S. Pat. No. 6,622,721 to Vedrine, et al. In these prior art devices, a user exerts pressure on a plunger to urge the liquid out of the sprayer.

To properly administer the medicament through a nasal passageway, the spray nozzle must generate a spray. To achieve a therapeutically effective spray, the plunger must be actuated at a certain speed that is sufficient. If the delivery speed of the medicament through the nozzle does not exceed the threshold speed, the liquid is ejected in a stream or drops instead of a spray. Furthermore, the inventors of the present invention have discovered that it can be difficult to ensure that the proper amount of the medicament has been delivered using the prior art devices.

SUMMARY OF THE INVENTION

The present invention relates to medical device for intranasal delivery of a medicament. The medicament may be any type of medicament suitable for nasal administration and delivery in the form of a spray. The present invention further ensures that a complete dosage of the medicament is delivered.

According to an embodiment of the invention, the medical device includes a body, a container received in the body and holding a medicament to be administered, and a pusher that is actuatable to deliver the medicament out of the container. More specifically, the present invention relates to a delivery device for delivery of a medicament to a user including a container defining a reservoir storing the medicament, a body in which the container is received, a spray nozzle arranged on one of the body and the container for receiving medicament expelled from the container, and a pusher actuatable for pushing the medicament from the container reservoir through the nozzle, said pusher being movable from a rest position to a fully activated position relative to said body in response to an actuating force. The assembly is particularly applicable to nasal syringes where it is desirable to deliver the medicament in the form of a spray.

According to the invention, at least one interlock retains the pusher in said rest position until the actuating force applied to the pusher exceeds a threshold value, the at least one interlock releasing the pusher when the actuating force exceeds the threshold force, and the threshold force being sufficiently large to ensure that the pusher is moved at a speed that generates a spray of the medicament from said nozzle upon release of said pusher by the at least one interlock. The at least one interlock includes a pair of interlocking parts respectively arranged on the pusher and the body to block movement of the pusher relative to the body. The pair of interlocking parts includes a movable interlocking part and the other interlocking part. The movable interlocking part is resiliently movable when the threshold actuating force is exceeded to unblock the movement of the pusher relative to the body.

In one embodiment, the spray nozzle is mounted on the container and the container is held in the body by a snap fit connection between the spray nozzle and the body. In an alternative embodiment, the spray nozzle is mounted on said body and the container connects to the nozzle when the container is inserted into the body. The snap fit connection may be effected in that the container is a syringe having a flange and the container is held in the body by a snap fit connection between the flange and the body.

In a further embodiment, the container includes a plunger disposed in the reservoir and the pusher includes a stem for pushing the plunger during movement toward the activated position. A gap may be present between the stem and the plunger when the pusher is at the rest position prior to activation of said device. This gap prevents inadvertent actuation of the device during storage and shipping.

Instead of a plunger, the container may include a roller ball or roller cylinder that squeezes a diaphragm or envelope to deliver the medicament through the nozzle. Although a plunger, rolling ball, and rolling cylinder are mentioned, the mechanism used to deliver the medicament through the nozzle may comprise any known or hereafter developed methods and/or devices to achieve the results.

According to an embodiment, the movable interlocking part is disposed on a resilient arm. Further, the movable interlocking part slides on a surface during movement of the pusher from the end position to the fully activated position. The other interlocking part is part of the surface. The resilient arm bends as the movable interlocking part slides over the other interlocking part requiring an increasing actuating force until the actuating force reaches the threshold actuating force and the movable interlocking part clears the other interlocking part.

In a specific embodiment, the pusher comprises the resilient arm and said movable interlocking part is disposed on the resilient arm. In this embodiment, the surface is disposed on the body.

In another specific embodiment, the body comprises at least one pair of rails comprising first and second rails extending between the front part of the body and a rear part of the body. A longitudinal space is defined between the first and second rails and the resilient arm is arranged in the longitudinal space. In this embodiment, the surface is arranged on one of the first and second rails. Further, the movable interlocking part is a boss disposed proximate a free end of the resilient arm and extends laterally out of the longitudinal space and over the surface on the one of said first and second rails such that said boss rests resiliently on the surface. The surface faces away from the container held in the body, and the boss projects in a direction perpendicular to a plane in which the resilient arm is movable.

In another embodiment, the at least one interlock includes first and second interlocks disposed on opposing sides of the container, each said first and second interlocks comprising the above-described pair of interlocking parts. In this embodiment, the first and second interlocks respectively further include first and second resilient arms connected to the pusher and respective first and second surfaces disposed on the body on which said movable interlocking parts slide. As described above, the other interlocking parts of said first and second interlocks being part of said first and second surfaces, respectively. The body has a first pair of rails including first and second rails and a second pair of rails comprising third and fourth rails. The first and second pairs of rails are connected between the front part of the body and a rear part of said body. The first resilient arm is arranged in a longitudinal space between the first and second rails and the second resilient arm is arranged in a longitudinal space between the third and fourth rails. In this embodiment, the first surface is disposed on one of the first and second rails and the second surface is disposed on one of the third and fourth rails. In a preferred embodiment, the various parts of the first and second interlocks are arranged on diametrically opposed sides of the delivery device.

DETAILED DESCRIPTION OF THE PRESENTLY PREFERRED EMBODIMENTS

Figure 1:
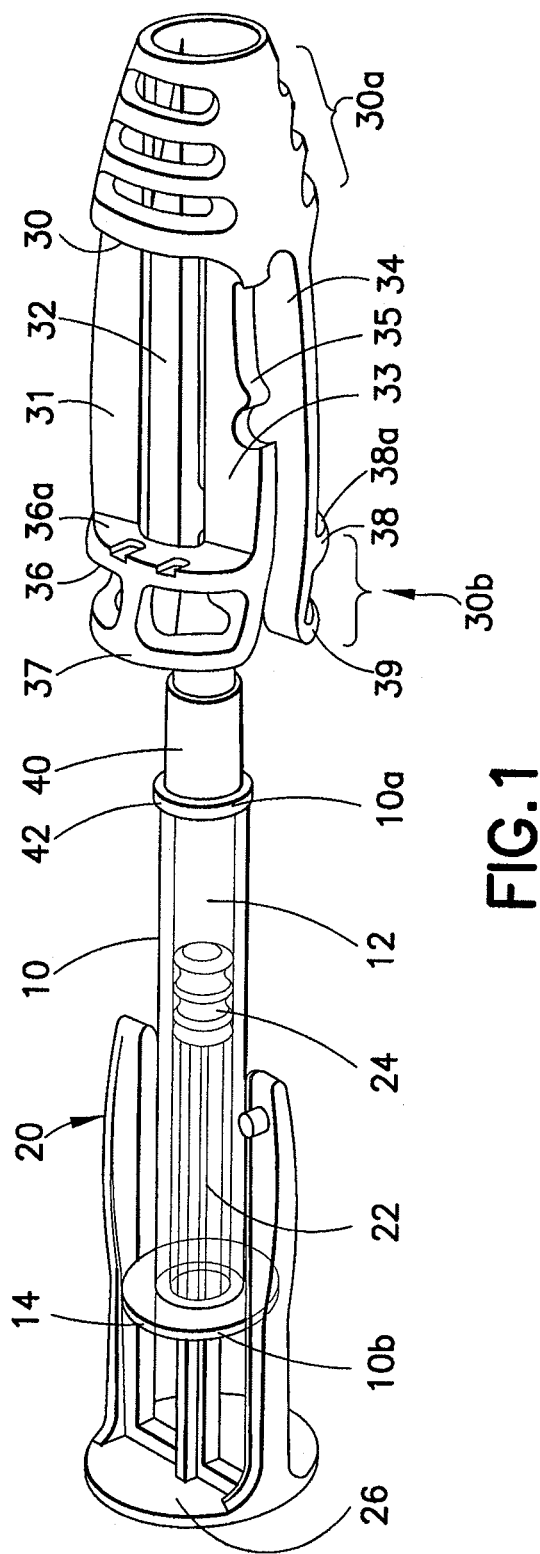
FIG. 1 is an exploded perspective view of a nasal delivery device according to an embodiment of the present invention.

An embodiment of a nasal delivery device 100 according to the present invention is shown in FIGS. 1. According to the embodiment, a container 10 includes a reservoir with a medicament to be dispensed. The medicament is intended to refer to any drug substance, vaccine, or other liquid substance that is intended to be administered. In a preferred embodiment, the medicament is to be administered as a spray, preferably through a nasal passageway. A spray nozzle 40 is arranged at front end 10a of the container 10 to generate a spray when the medicament is urged therethrough. The container 10 is held in a body 30. In one embodiment, the container 10 is tubular and comprises a syringe barrel that provides the primary container for the medicament such as an Accuspray™ barrel, manufactured by Becton Dickenson, Franklin Lakes, N.J. However, the container 10 may alternatively be any known or hereafter developed container which can be designed as one piece with the spray nozzle 40 comprising an integral part thereof, or can be designed as a separate piece with the spray nozzle 40 attached thereto, such as by a luer connection. As a further alternative, the spray nozzle 40 may be fixed to the body 30 so that the container 10 attaches to the spray nozzle 40 upon insertion of the container 10 in the body 30.

The container 10 may be snap fit into the body 30, for example, by a flange 14 and/or by an annular rib 42 (see, e.g., FIGS. 9 and 10) on the spray nozzle 40, or any other protrusion, projection, or boss on the container 10 and/or spray nozzle 40. Alternatively, the protrusion, projection, or boss may be disposed on the body 30 and interact with a recess, groove or other feature on the container 10 and/or nozzle 40 to effect a snap fit. When the container 10 is fully inserted in the body, at least the spray nozzle 40 extends through a front end 30a of the body 30.

Figure 4:
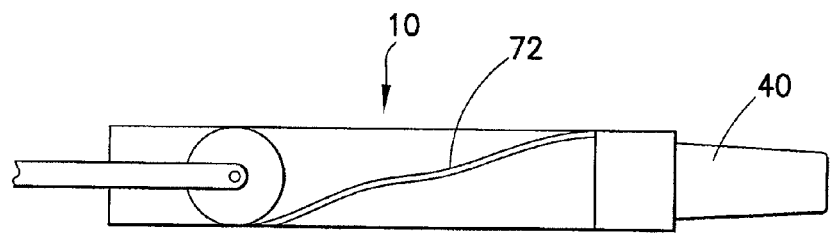
FIG. 4 is a side view of a container of the nasal delivery device according to another embodiment.
Figure 5:
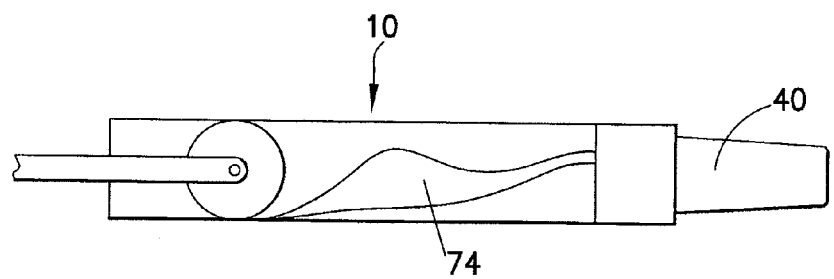
FIG. 5 is a side view of a container of the nasal delivery device according to yet another embodiment.

A pusher stem 22 of a pusher 20 is inserted through a rear end 10b of the container 10 and extends along a longitudinal axis that coincides with a longitudinal axis of the tubular container 10. The pusher 20 pushes a plunger 24 toward the front end 10a of the container 10 to deliver the medicament through the spray nozzle 40. A thumb pad 26 is connected to the rear end of the pusher 20, allowing a user to apply actuating pressure through the pusher 20 to the plunger 24. Instead of a plunger, the pusher 20 may include a roller cylinder or roller ball that acts on a flexible diaphragm or envelope to squeeze the medicament out of the container as shown in FIGS. 4 and 5. In the FIG. 4 embodiment, the container 10 includes a diaphragm 72. In the FIG. 5 embodiment, the container 10 includes an envelope 74 holding the medicament.

Figure 2:
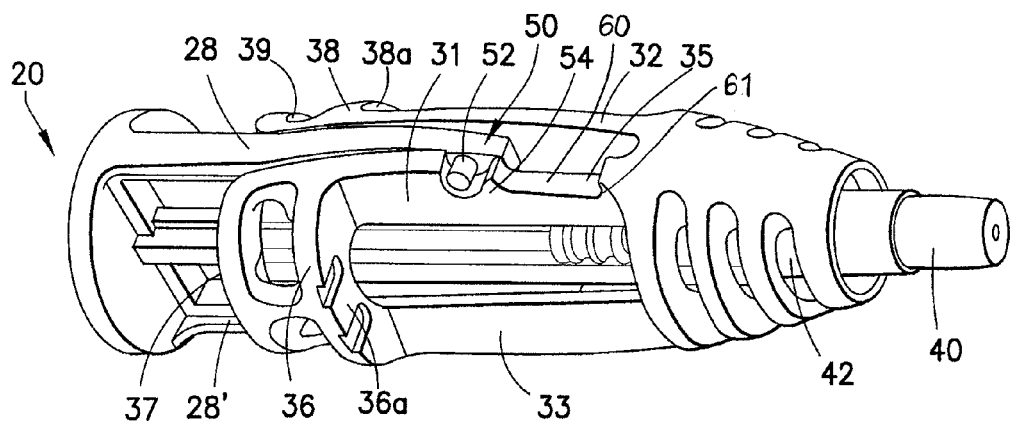
FIG. 2 is a perspective view of a nasal delivery device according to another embodiment of the present invention in a rest position.
Figure 3:
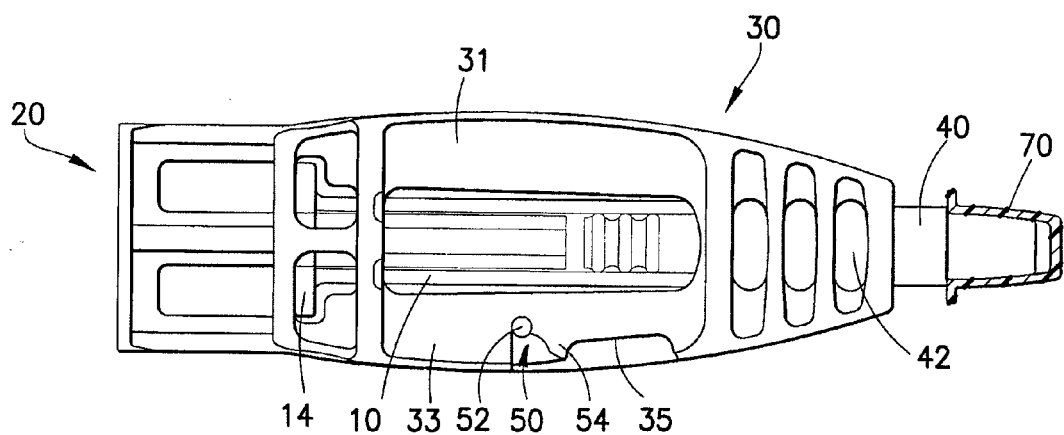
FIG. 3 is a side view of the nasal delivery device of FIG. 1.
Figure 8:
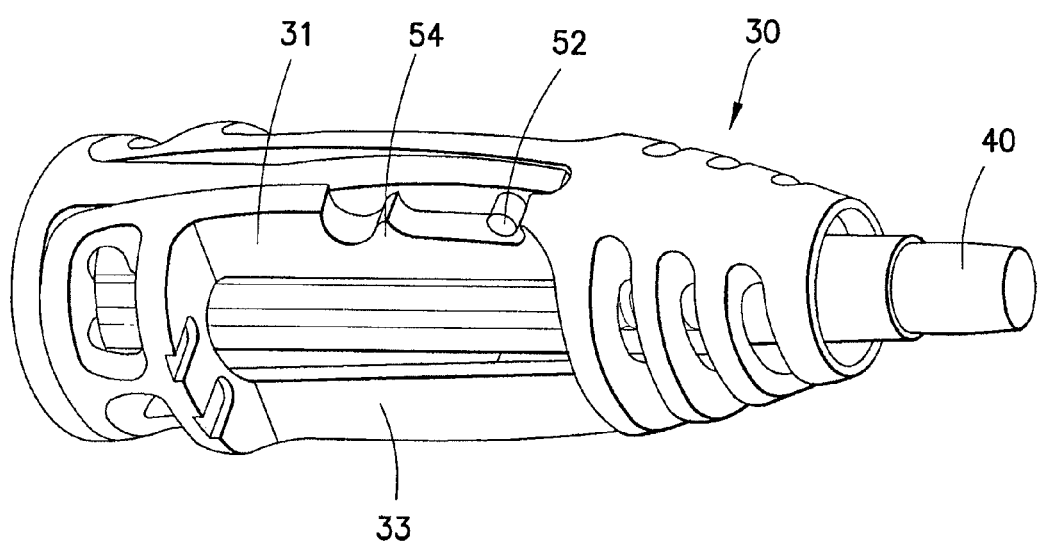
FIG. 8 is a perspective view of the nasal delivery device of FIG. 2 in the fully activated position.

A shown in FIGS. 2, 3, and 8, the front end 30a of the body 30 surrounds the front end 10a of the container 10. Four longitudinal rail elements 31, 32, 33, 34 connect the front end 30a to the rear end 30b of the body 30. Rails 31 and 33 are connected to each other at the rear end 30b by a tab 36 extending laterally and a stop 37. Similarly, rails 32 and 34 are connected to each other at the rear end 30b of the body 30 by a tab 38 and a stop 39. The tabs 36, 38 include features, i.e., indentations or a knurled surface, on the front ends 36a, 38a thereof that facilitate gripping by a user for applying an actuating force as described in more detail below.

As is known, if liquid passes through a nozzle at a very slow speed, a stream or drop of liquid is generated instead of a spray. Accordingly, a minimum or threshold activation speed must be exceeded so that the device generates a spray of the medicament instead of a stream. To ensure that the user uses adequate force so that a spray is generated, an interlock 50 is arranged between the pusher 20 and the body 30. The interlock 50 includes a first interlocking part 52 disposed on the pusher and a second interlocking part 54 disposed on the body 30.

Prior to use of the nasal delivery device, the pusher 20 is blocked in an end or rest position by the interlock 50. The first and second interlocking parts 52, 54 are interlocked, as shown in FIGS. 2, 3, 6, and 9 in the rest position of the pusher 20. As explained in more detail below, the pusher 20 is movable from the rest position to a fully activated position to eject the medicament through the spray nozzle 40. The second interlocking part 54 is arranged on a track 35 on rail 31 of the body 30. The first interlocking part 52 is a track follower that slides on the track 35 when the pusher 20 moves toward the fully activated position to push the plunger 24 toward the front end 10a of the container 10. The first interlocking part 52 is a boss or peg arranged on a flexible arm 28 on the pusher 20. The track 35 includes the second interlocking part 54, a movement path 60, and a stop 61 (see FIG. 2). The flexible arm 28 is arranged between rails 31 and 32 and is configured so that the resilient arm 28 resiliently bends away from the container held in the body 30 as the first interlocking part 52 slides over the second interlocking part 54 when the pusher 20 moves out of the rest position. The first and second interlocking parts 52, 54 are mutually disposed so that the actuating force applied on the thumb pad required for the first interlocking part 52 to clear the second interlocking part 54 is greater than the actuating force required to generate a spray of the medicament from the spray nozzle once the first interlocking part 52 clears the second interlocking part 54. After clearing the second interlocking part 54, the first interlocking part slides along the remainder of the track 35 without obstructions, so that the force applied to the thumb pad 26 pushes the medicament through the spray nozzle 40. The first interlocking part 52 reaches the stop 62 when the pusher reaches the fully activated position.

Figure 2A:
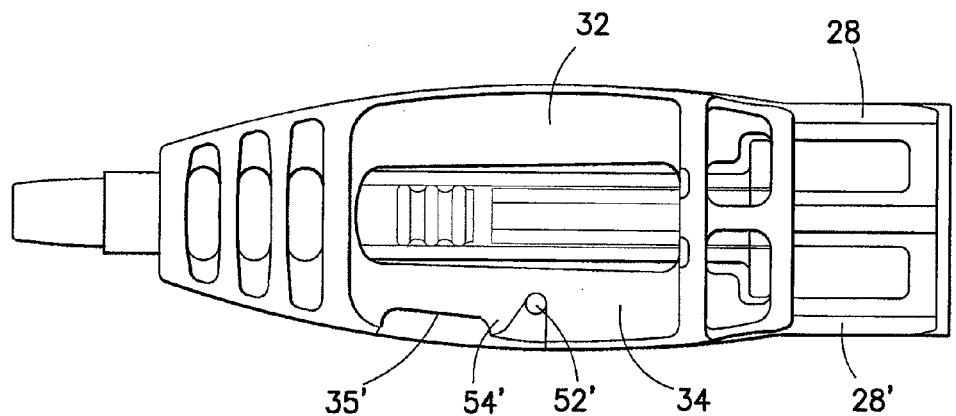
FIG. 2a shows a side of the nasal delivery device of FIG. 2 with a second interlock.

In FIG. 2a, a second interlock 50' with first and second interlocking parts 52', 54' arranged on flexible arm 28' and a track 35' on rail 34 (the second interlock is not fully visible in FIG. 2). More specifically, another first interlocking part 52' is arranged on the flexible arm 28' and another second interlocking part 54' is arranged on track 35' on rail 34.

FIGS. 1 and 3 show the track 35 on rail 33 instead of rail 31. In this embodiment, the second interlock is arranged on rail 32. Thus, the tracks 35 and the second interlocking parts 54 of the interlock and second interlock can be arranged on rails 31 and 34 (FIG. 2) or on rails 32 and 33 (FIGS. 1 and 3).

In one embodiment, a gap is present between the pusher stem 22 and the plunger 24 when the pusher 20 is in the interlocked position as shown in FIG. 3. This gap prevents inadvertent application of any pressure on the medicament during storage and shipping. The gap may also be used to ensure that none of the therapeutic fluid escapes while the first interlocking part 52 clears the second interlocking part 54.

Figure 6:
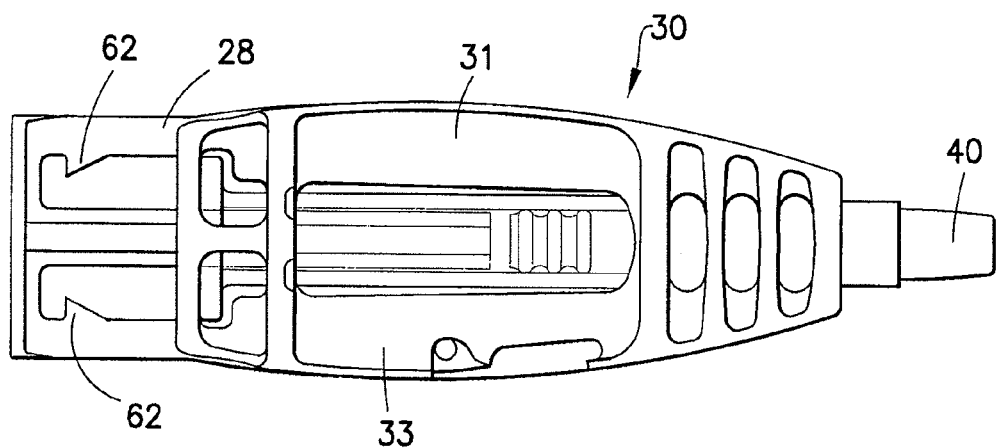
FIG. 6 is a side view of a nasal delivery device having a snap feature according to another embodiment of the invention.
Figure 7:
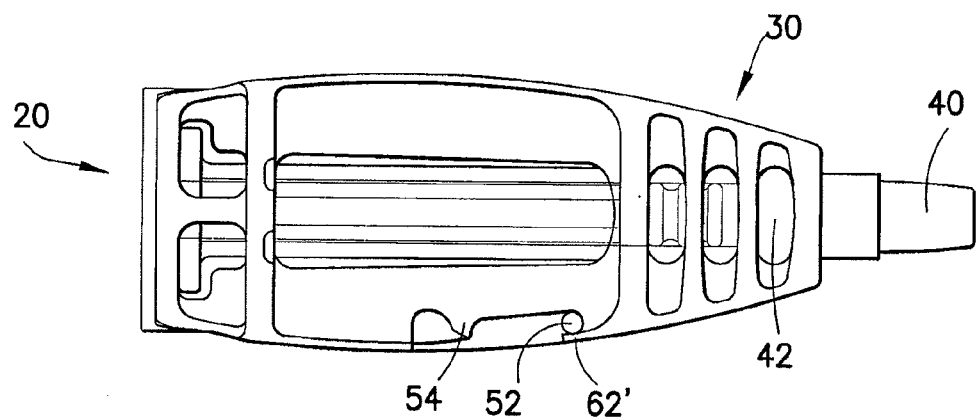
FIG. 7 is a side view of the nasal delivery device of FIG. 1 in the fully activated position.

The pusher 20 may comprise snap projections 62 on resilient arms 28, 28a, which snap into a recess or other feature on the body 30 when the pusher 20 enters the fully inserted position (see FIG. 6). The snap projection 62 provides a tactile and/or audible confirmation that the entire dose has been delivered through the spray nozzle 40. As an alternative, the first interlocking part 52, or another projection arranged proximate the front of the pusher 20 can be arranged to snap into a recess 62', as shown in FIG. 7.

Figure 9:
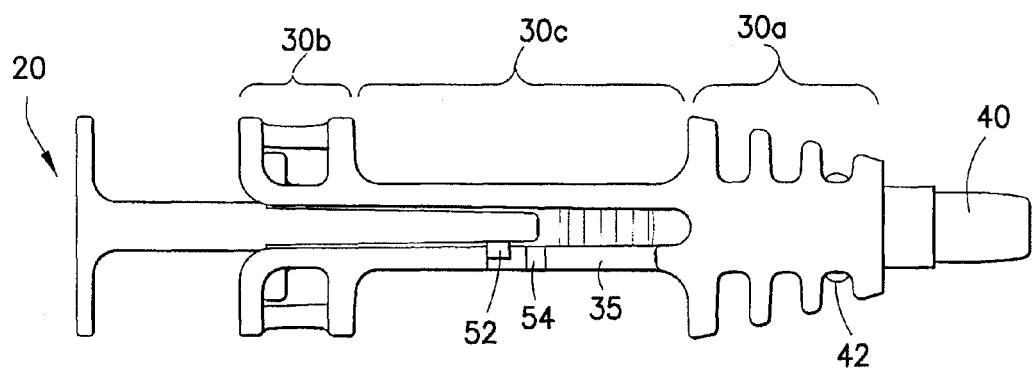
FIGS. 9 and 10 are plan views of the nasal delivery device of FIG. 2 in the rest and fully activated positions, respectively.
Figure 10:
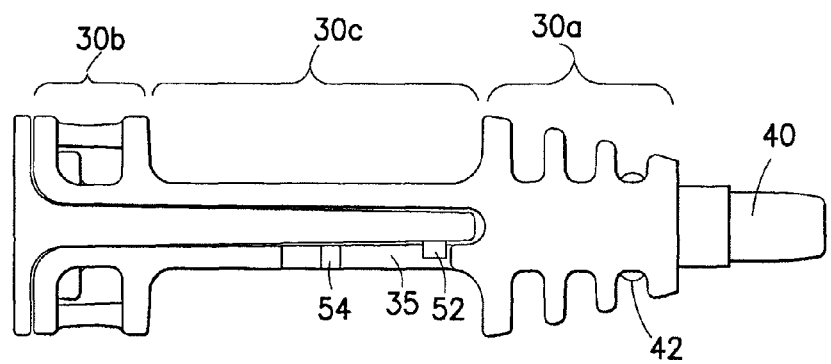

As shown in FIGS. 1-3, the container 10 is visible through body 30. As further shown in FIG. 3, a cap 70 may be placed on the spray nozzle to prevent dirt, dust, or other contaminants from reaching the nozzle during storage and/or shipping. FIGS. 8 and 9 show side views of the nasal delivery device in the rest and fully activated position of the pusher 20, respectively. As is readily apparent from FIGS. 9 and 10, the body 30 is easy to manufacture by molding because the body has no undercuts. The body 30 can be molded by a two-part mold which are clamped together from above and below the plane of FIGS. 9 and 10. The features on the tabs 36, 38 facilitating a grip by the user can be added after molding.

Figure 13:
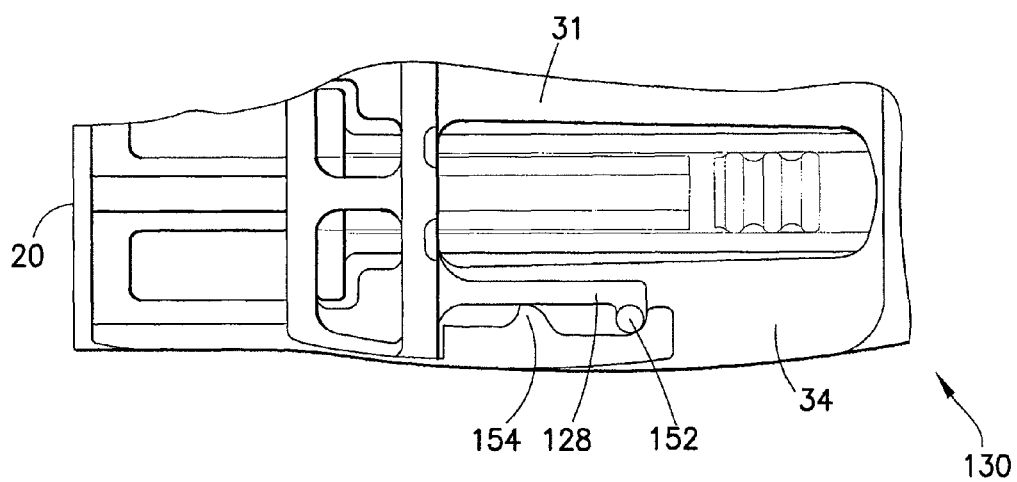
FIG. 13 is a side view of a further embodiment of the nasal delivery device.

In an alternative embodiment shown in FIG. 13, the first interlocking device 152 and resilient arm 128 are arranged on the body 130. The surface and second interlocking device 154 are disposed on the pusher 120.

Figure 11A:
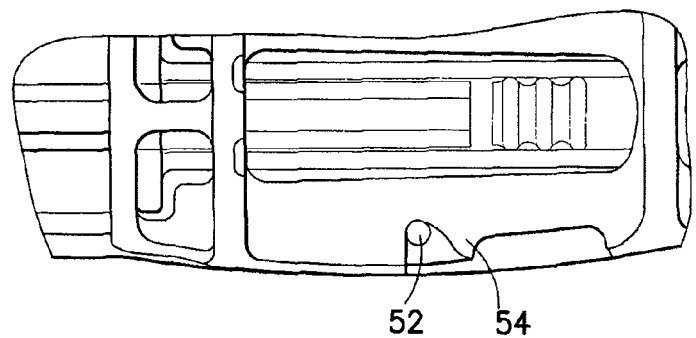
FIGS. 11a-11d are detailed views of an interlock of the nasal delivery device of FIG. 1 at four different positions during use.
Figure 11B:
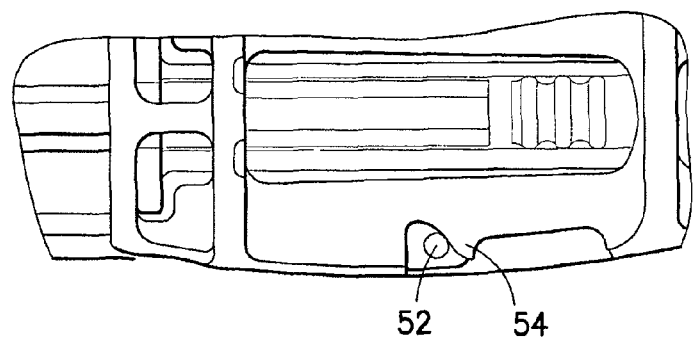
Figure 11C:
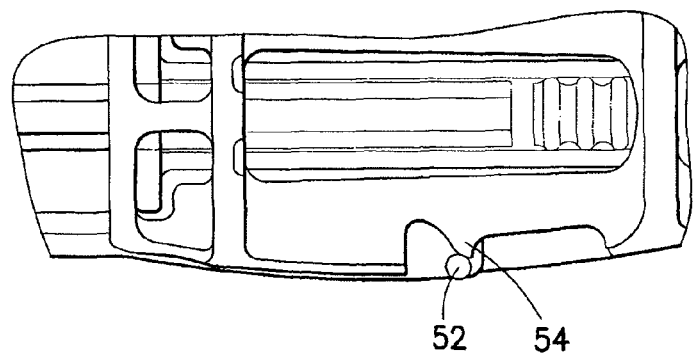
Figure 11D:
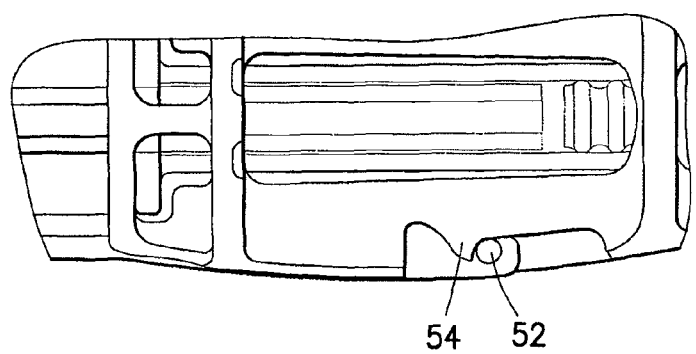
Figure 14:
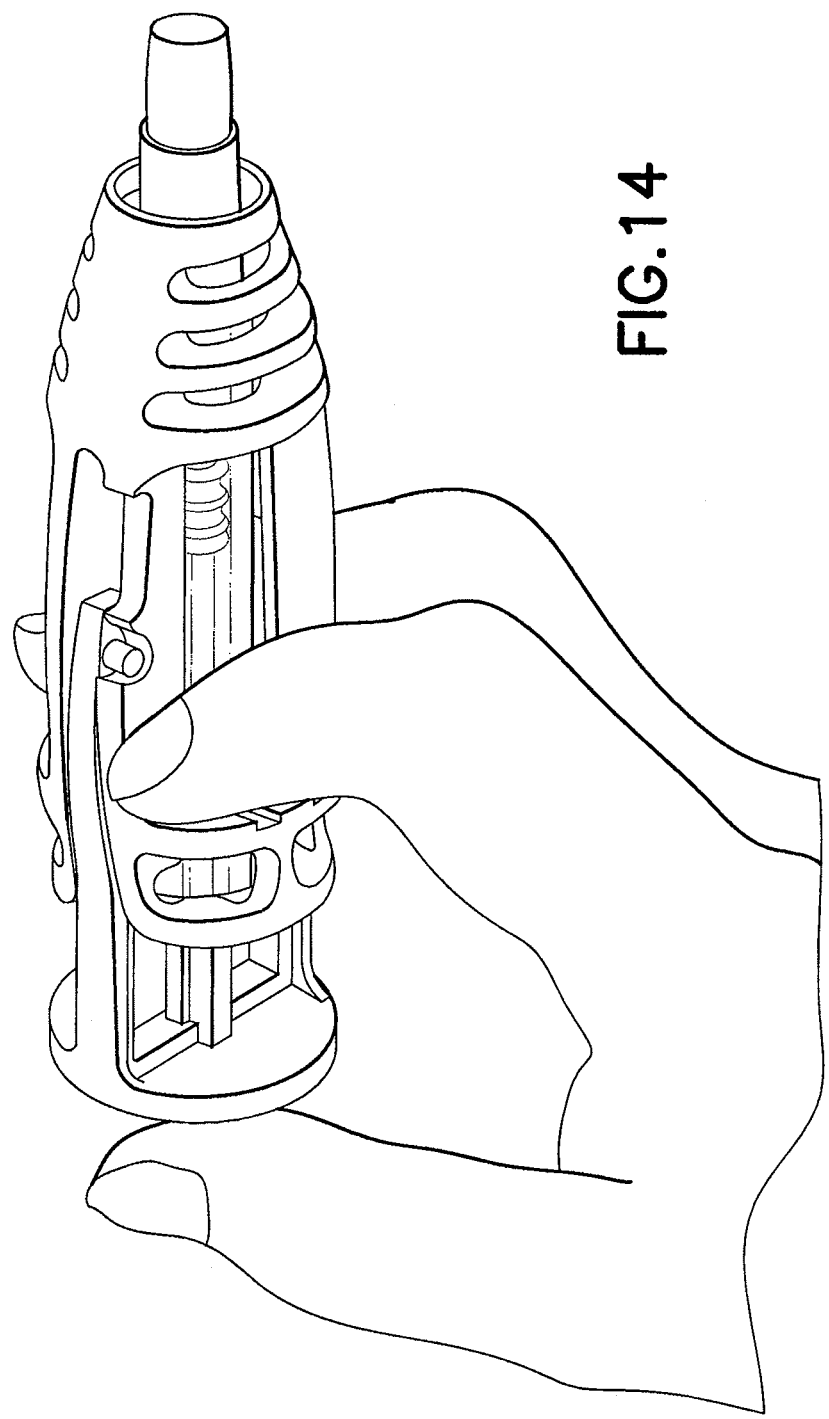
FIG. 14 is a perspective view of the nasal delivery device being grasped by a user.

A description of an exemplary usage of the device of FIGS. 1-10 is now provided with reference to FIGS. 11a-11d, 12 and 14. It should be understood by a person of ordinary skill in the art that the following description is provided as an illustrative and nonlimiting example. Users of the device may include health care professionals or other caregivers administering the medicament to patient or the patients themselves. The user receives the inventive device prefilled with a desired dosage of medicament. If the cap 70 is present, the user removes the cap 70 from the spray nozzle 40. After removing the cap 70, the user grasps the nasal spray device with a thumb and two fingers as shown in FIG. 14. The user then inserts the spray nozzle 40 into the patient's nasal cavity. At this point, the device, is still in the rest position shown in FIG. 11a. The user then begins applying pressure to the pusher 20. In FIG. 11b, the pusher 20 is moved by the user, but the device is not yet activated because the force applied has not reached the threshold to clear the interlock between the first and second interlocking parts 52, 54. Once the force reaches the threshold as shown in FIG. 11c, the first interlocking part 52 clears the second interlocking part 54. Once the first interlocking part 52 is cleared (FIG. 11d) the actuating force on the pusher 20 moves the pusher forward and pushes the medicament through the nozzle and the generation of spray is started. The pusher 20 is pushed continuously until the pusher 20 reaches the fully activated position as shown in FIG. 5.

Figure 12:
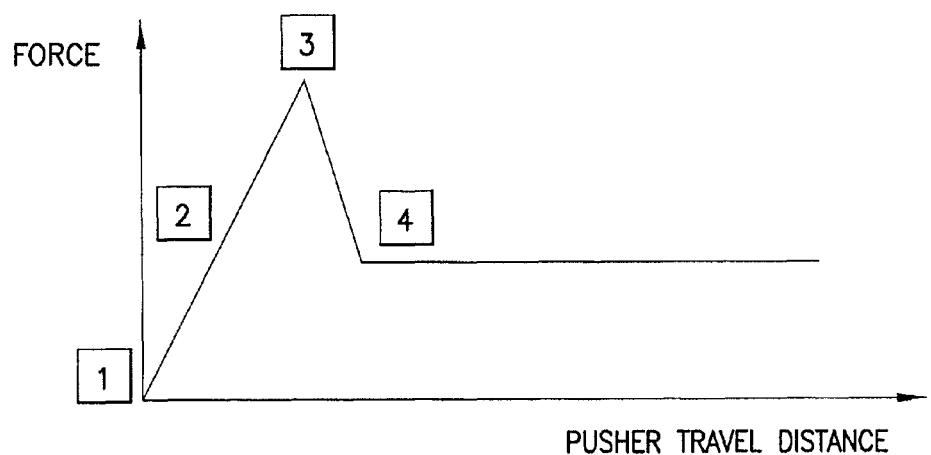
FIG. 12 is a graph showing the actuating force applied to the nasal delivery device over the travel distance of the pusher.

FIG. 12 shows the actuating force at each of the stages depicted in FIGS. 11a-11d. The maximum force is present immediately before the first interlocking part 52 clears the second interlocking part 54. This ensures that once the first interlocking part 52 clears the second interlocking part 54, the proper force is applied to generate a spray from the nozzle 40.

The invention claimed is:

1. A delivery device for delivery of a medicament to a user, comprising:
   a tubular reservoir for containing the medicament;
   a body sized and shaped to receive at least a part of said reservoir;
   a spray nozzle arranged on one of said body and said reservoir, said nozzle providing a path for the medicament to be expelled from said reservoir;
   a pusher defining a longitudinal axis and being actuatable for causing the medicament to be expelled from said reservoir through said nozzle, said pusher being movable from a rest position to a fully activated position relative to said body in response to an actuating force;
   a dose control apparatus for ensuring that the medicament is delivered by said device, said dose control apparatus comprising a track defined on said body and a track follower defined on said pusher, said track follower further comprising a peg defined on a flexible arm of said pusher, said track further comprising an interlock defining an interlock surface and a movement path and a stop, said interlock releasably receiving and retaining said track follower when said pusher is in said rest position, said pusher being retained in said rest position until a user applies said actuating force to said pusher thereby causing said track follower to engage said interlock surface, said interlock surface impeding movement of said track follower and maintaining said pusher in said rest position until said actuating force meets or exceeds a predetermined value, thereafter said flexible arm of said pusher being deflected in a direction transverse to said longitudinal axis of said pusher and said track follower overcoming said interlock surface and said track follower being movable along said track, said pusher being movable by a user from said rest position to said activated position to cause the medicament to be expelled from said reservoir through said nozzle.

2. The delivery device of claim 1, wherein said spray nozzle is mounted on said reservoir, and said reservoir is held in said body by a snap fit between said spray nozzle and said body.

3. The delivery device of claim 1, wherein said spray nozzle is mounted on said body.

4. The delivery device of claim 1, wherein said reservoir is a syringe having a flange and said reservoir is held in said body by a snap fit between said flange and said body.

5. The delivery device of claim 1, further comprising a plunger disposed in said reservoir, said pusher comprising a stem for pushing said plunger during movement toward said activated position.

6. The delivery device of claim 5, wherein a gap is defined between said stem and said plunger when said pusher is at said rest position prior to activation of said device.

7. The delivery device of claim 1, wherein said flexible arm bends as said track follower slides over said interlocking surface requiring an increasing actuating force until said track follower clears said interlocking surface.

8. The delivery device of claim 7, wherein the body comprises at least one pair of rails comprising first and second rails extending between a front part of said body and a rear part of said body and defining a longitudinal space therebetween, the flexible arm being arranged in said longitudinal space and said track being arranged on one of said first and second rails.

9. The delivery device of claim 8, wherein said peg extends laterally out of the longitudinal space and over said one of said first and second rails such that said peg rests resiliently on said track.

10. The delivery device of claim 9, wherein said track faces away from said reservoir.

11. The delivery device of claim 10, wherein said peg projects in a direction perpendicular to a plane in which said flexible arm is movable.

12. The delivery device of claim 1, wherein said track include first and second tracks disposed on opposing sides of said body and said track follower includes first and second track followers on first and second flexible arms of said pusher.

13. The delivery device of claim 12, said body having a first pair of rails including first and second rails and a second pair of rails comprising third and fourth rails, said first and second pairs of rails being connected between said front part of said body and a rear part of said body, said first flexible arm being arranged in a longitudinal space between said first and second rails and said second flexible arm being arranged in a longitudinal space between said third and fourth rails, and said first track being disposed on one of said first and second rails and said second track being disposed on one of said third and fourth rails.

14. The delivery device of claim 1, wherein said delivery device is a monodose delivery device in that the movement of the pusher from the rest position to the fully activated position causes a single complete dose of the medicament to be delivered through the nozzle.

15. The delivery device of claim 14, further comprising a snap projection that provides at least one of a tactile and audible indication when the pusher enters the fully activated position, thereby providing confirmation to a user that an entire dose of the medicament has been delivered.

16. A delivery device for delivery of a medicament to a user, comprising:
a tubular reservoir for containing the medicament;
a body sized and shaped to receive at least a part of said reservoir;
a spray nozzle arranged on one of said body and said reservoir, said nozzle providing a path for the medicament to be expelled from said reservoir;
a pusher defining a longitudinal axis and being actuatable for causing the medicament to be expelled from said reservoir through said nozzle, said pusher being movable from a rest position to a fully activated position relative to said body in response to an actuating force;
a dose control apparatus for ensuring that the medicament is delivered by said device, said dose control apparatus comprising a track defined on said body and a track follower defined on said pusher, said track follower further comprising a peg defined on a flexible arm of said pusher, said track further comprising an interlock defining an interlock surface and a movement path and a stop, said interlock releasably receiving and retaining said track follower when said pusher is in said rest position, said pusher being retained in said rest position until a user applies said actuating force to said pusher thereby causing said track follower to engage said interlock surface, said interlock surface impeding movement of said track follower and maintaining said pusher in said rest position until said actuating force meets or exceeds a predetermined value, thereafter said flexible arm of said pusher being deflected in a direction transverse to said longitudinal axis of said pusher and said track follower overcoming said interlock surface and said track follower being movable along said track, said pusher being movable by a user from said rest position to said activated position to cause the medicament to be expelled from said reservoir through said nozzle,
wherein said flexible arm bends as said track follower slides over said interlocking surface requiring an increasing actuating force until said track follower clears said interlocking surface,
further wherein the body comprises at least one pair of rails comprising first and second rails extending between a front part of said body and a rear part of said body and defining a longitudinal space therebetween, the flexible arm being arranged in said longitudinal space and said track being arranged on one of said first and second rails, and
further wherein said peg extends laterally out of the longitudinal space and over said one of said first and second rails such that said peg rests resiliently on said track.

17. The delivery device of claim 16, wherein said track faces away from said reservoir.

18. The delivery device of claim 17, wherein said peg projects in a direction perpendicular to a plane in which said flexible arm is movable.

19. A delivery device for delivery of a medicament to a user, comprising:
a tubular reservoir for containing the medicament;
a body sized and shaped to receive at least a part of said reservoir;
a spray nozzle arranged on one of said body and said reservoir, said nozzle providing a path for the medicament to be expelled from said reservoir;

a pusher defining a longitudinal axis and being actuatable for causing the medicament to be expelled from said reservoir through said nozzle, said pusher being movable from a rest position to a fully activated position relative to said body in response to an actuating force;

a dose control apparatus for ensuring that the medicament is delivered by said device, said dose control apparatus comprising a track defined on said body and a track follower defined on said pusher, said track follower further comprising a peg defined on a flexible arm of said pusher, said track further comprising an interlock defining an interlock surface and a movement path and a stop, said interlock releasably receiving and retaining said track follower when said pusher is in said rest position, said pusher being retained in said rest position until a user applies said actuating force to said pusher thereby causing said track follower to engage said interlock surface, said interlock surface impeding movement of said track follower and maintaining said pusher in said rest position until said actuating force meets or exceeds a predetermined value, thereafter said flexible arm of said pusher being deflected in a direction transverse to said longitudinal axis of said pusher and said track follower overcoming said interlock surface and said track follower being movable along said track, said pusher being movable by a user from said rest position to said activated position to cause the medicament to be expelled from said reservoir through said nozzle, wherein said tracks include first and second tracks disposed on opposing sides of said body and said track follower includes first and second track followers on first and second flexible arms of said pusher, and said body having a first pair of rails including first and second rails and a second pair of rails comprising third and fourth rails, said firt and second pairs of rails being connected between said front part of said body and a rear part of said body, said first flexible arm being arranged in a longitudinal space between said first and second rails and said second flexible arm being arranged in a longitudinal space between said third and fourth rails, and said first track being disposed on one of said first and second rails and said second track being disposed on one of said third and fourth rails.

* * * * *